United States Patent
Emmel et al.

(10) Patent No.: US 7,501,075 B2
(45) Date of Patent: Mar. 10, 2009

(54) SYNTHESIS AGENT CONTAINING METHYLLITHIUM/LITHIUM BROMIDE, AND PROCESS FOR THE PREPARATION THEREOF

(75) Inventors: Ute Emmel, Frankfurt am Main (DE); Peter Rittmeyer, Sulzbach/Taunus (DE); Ulrich Wietelmann, Friedrichsdorf (DE); Rainer Aul, Rodgau (DE)

(73) Assignee: Chemetall GmbH, Frankfurt am Main (DE)

( * ) Notice: Subject to any disclaimer, the term of this patent is extended or adjusted under 35 U.S.C. 154(b) by 588 days.

(21) Appl. No.: 11/209,258

(22) Filed: Aug. 23, 2005

(65) Prior Publication Data

US 2006/0049379 A1 Mar. 9, 2006

(30) Foreign Application Priority Data

Sep. 6, 2004 (DE) .................. 10 2004 043 501

(51) Int. Cl.
*C09K 3/00* (2006.01)
*C07F 1/02* (2006.01)

(52) U.S. Cl. .............................. 252/182.3; 252/182.12; 252/182.16; 252/182.29; 502/152; 502/169

(58) Field of Classification Search .............. 252/182.3, 252/182.16
See application file for complete search history.

(56) References Cited

U.S. PATENT DOCUMENTS

| 4,976,886 | A | | 12/1990 | Morrison et al. | |
|---|---|---|---|---|---|
| 5,002,689 | A | | 3/1991 | Mehta et al. | |
| 5,100,575 | A | * | 3/1992 | Hatch et al. | 252/182.3 |
| 5,141,667 | A | | 8/1992 | Morrison et al. | |
| 5,171,467 | A | * | 12/1992 | Mehta et al. | 252/182.3 |
| 5,320,774 | A | | 6/1994 | Mehta et al. | |
| 5,677,543 | A | | 10/1997 | Weiss et al. | |
| 6,495,064 | B2 | * | 12/2002 | Weiss et al. | 252/182.14 |
| 6,770,763 | B2 | * | 8/2004 | Magnus et al. | 548/550 |
| 2003/0236401 | A1 | * | 12/2003 | Magnus et al. | 540/363 |
| 2006/0241299 | A1 | * | 10/2006 | Volante et al. | 546/16 |
| 2007/0276163 | A1 | * | 11/2007 | Evans et al. | 568/558 |

FOREIGN PATENT DOCUMENTS

| DE | 39 05 857 C2 | 9/1989 |
|---|---|---|
| DE | 39 05 857 C3 | 9/1989 |
| DE | 39 43 841 C2 | 9/1989 |
| DE | 44 24 222 C1 | 9/1995 |
| DE | 38 56 437 T2 | 6/2001 |
| EP | 07 53 520 | 1/1997 |
| EP | 0 673 941 B1 | 10/2000 |

* cited by examiner

*Primary Examiner*—Joseph D Anthony
(74) *Attorney, Agent, or Firm*—Fulbright & Jaworski L.L.P.

(57) ABSTRACT

A synthesis agent containing methyllithium and lithium bromide is described, in which MeLi and LiBr are dissolved in a solvent of the general formula (I)

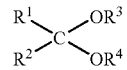

wherein $R^1$ and $R^2$ independently of one another are H, methyl (Me) or ethyl (Et), and $R^3$ and $R^4$ are Me or Et, the molar ratio of LiBr to MeLi being at least 0.7 and not more than 1.5 and the methyllithium concentration being at least 4 wt. %.

29 Claims, No Drawings

SYNTHESIS AGENT CONTAINING METHYLLITHIUM/LITHIUM BROMIDE, AND PROCESS FOR THE PREPARATION THEREOF

This application claims priority from DE 102004043501.4 filed Sep.6,2004, herein incorporated by reference in its entirety.

The invention relates to a synthesis agent containing methyllithium/lithium bromide, and to a process for the preparation thereof.

Methyllithium is used as a reagent in the production of pharmaceutical products, such as vitamins or steroids, and in special synthesis steps, such as reactions of the carbene type for the preparation of allenes and alkoxycyclopropanes, methylating reactions for the preparation of alkenyllithium and steroidal alkenyl compounds, reduction reactions of various transition metal halides, such as $PdCl_2$ to Pd(0), the preparation of methyllithium cuprates for 1,4-conjugated additions or for the preparation of other organometallic compounds, such as $Me_2Mg$, $MeTi(NEt_2)_3$, $Me_3Al$, $Me_3Al$, $Me_3As$ or $Me_3Ga$.

Methyllithium is available commercially in the form of an approximately 5% solution in diethyl ether or in the form of an approximately 6% solution in diethyl ether, which contains approximately 10% lithium bromide as complex-forming stabiliser. These commercial forms of methyllithium in diethyl ether have only limited usability owing to the low flash point of diethyl ether. Other ethereal solutions of methyllithium have no commercial importance because on the one hand the concentration of methyllithium therein is very low (approximately 3 wt. %) and on the other hand their stability is inadequate (e.g. in THF or glycol ethers). In hydrocarbons and aromatic compounds, on the other hand, methyllithium is insoluble. A certain degree of solubility in aromatic compounds is achieved if the methyllithium-THF complex is used (max.3.74 wt. %). Accordingly, documents EP-A 02 285 374 and U.S. Pat. No. 5,171,467 disclose alkyllithium compounds in aromatic hydrocarbons which have been stabilised by a content of a Lewis base, such as tetrahydrofuran, and lithium halides. However, because these solutions tend to decompose by metallation of the aromatic hydrocarbon, dialkylmagnesium compounds are added. The content of active lithium compounds falls as a result to 2.6 wt. %, and the reactivity is affected by the presence of dialkylmagnesium compounds.

From EP 753 520 there are also known synthesis agents containing dissolved methyllithium, which synthesis agents contain methyllithium in a solvent of the general formula:

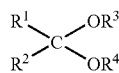

wherein $R^1$ and $R^2$ independently of one another are H, methyl (Me) or ethyl (Et) and $R^3$ and $R^4$ are methyl or ethyl.

These synthesis agents are prepared by
a) dispersing lithium powder or lithium granules in a solvent of the general formula I and adding methyl halide in metered amounts,
b) maintaining the reaction temperature in the range from 0 to 60° C. and
c) separating the resulting lithium halide from the methyllithium solution.

EP 753 520 further provides for the addition of up to 10% lithium bromide or lithium iodide in order to obtain a special synthesis agent suitable for stereochemical reactions. In Example 3, a solution containing 7.2% MeLi and 8.25% lithium bromide is described. This composition corresponds to a molar ratio LiBr:MeLi of approximately 0.29:1.

It is known that the selectivity of some organic reactions is greatly affected by the salt content, more precisely the molar ratio of lithium organyl to lithium salt.

Such effects are summarised by A. Loupy and B. Tchoubar ("Salt Effects in Organic and Organometallic Chemistry", VCH, Weinheim 1992) or C. Fehr (Angew. Chem. 1996, 108, 2726-2748). For example, the enantiomeric excess (ee) in the asymmetric protonation of prochiral enolates is affected by lithium salt additives (A. Yanagisawa et al., Synlett 1998, 174-176):

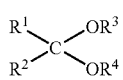

| $MX_n$ (equiv) | solvent[a] | % ee[b] |
|---|---|---|
| — | THF | 63 |
| — | $Et_2O$ | 74 |
| LiBr (1) | THF | 79 |
| LiBr (1) | $Et_2O$ | 83 |
| LiBr (2) | THF | 79 |
| LiBr (2) | $Et_2O$ | 85 |
| LiBr (5) | THF | 77 |
| LiBr (5) | $Et_2O$ | 90 |
| LiBr (10) | THF | 78 |
| LiBr (10) | $Et_2O$ | 88 |

[a]a small amount of hexane (Ca. 6 %) was contained in each solvent;
[b]determined by GC analysis with chiral column (Chiraldex ™ B-TA, astec).
(R)-Enriched ketone 6 was obtained in each case The object of the present invention is to overcome the disadvantages of the prior art and, in particular, to provide synthesis mixtures containing methyllithium in a solvent that is better to handle than diethyl ether, which synthesis mixtures have a highly selective action.

The object is achieved by a synthesis agent containing methyllithium and lithium bromide, in which MeLi and LiBr are dissolved in a solvent of the general formula (I)

$$\begin{array}{c} R^1 \\ R^2 \end{array}\!\!>\!\!C\!\!<\!\!\begin{array}{c} OR^3 \\ OR^4 \end{array} \quad (I)$$

wherein $R^1$ and $R^2$ independently of one another are H, methyl (Me) or ethyl (Et), and $R^3$ and $R^4$ are Me or Et, the molar ratio of LiBr to MeLi being at least 0.7 and not more than 1.5 and the methyllithium concentration being at least 4 wt. %.

In a preferred embodiment, the molar ratio of LiBr to MeLi is at least 0.8, particularly preferably at least 1.0.

The synthesis agent may comprise from 1 to 40 wt. % of one or more aromatic solvents, preference being given to benzene, toluene, ethylbenzene, xylene or cumene. However, it is also possible for the synthesis agent to contain no aromatic solvent.

The synthesis agent containing methyllithium and lithium bromide can be prepared by reaction of a methyl halide (M–Hal, where Hal=Cl or Br) with lithium metal, the reaction being carried out in a solvent of formula (I) and the lithium bromide being added to the resulting reaction mixture and/or being added to the solvent before the reaction. This means that, in the case where the amount of LiBr necessary to achieve a LiBr:MeLi stoichiometry has not already been introduced with the reaction solvent, the required amount of LiBr is added after the reaction and before or after separation of the insoluble constituents (unreacted lithium metal and insoluble lithium halide).

In a preferred embodiment of the present invention, methyl bromide is used as the methyl halide. It has been found, surprisingly, that the lithium bromide formed in the synthesis reaction according to $H_3C-Br + 2Li \rightarrow H_3C-Li + LiBr$ remains in solution even at high concentrations (>10 wt. %) and in a molar ratio LiBr:MeLi >>0.29, so that, after completion of the reaction according to the above equation, it cannot even be filtered off, as described in EP 753 520.

This procedure has the advantage that the filtration is substantially more simple compared with the process in which methyl chloride is used. The filter cake here consists only of excess lithium metal and small amounts of an insoluble white solid which contains elevated amounts of residual base, and accordingly constitutes inactive product. The relatively complex operation of washing the filtration residue is consequently unnecessary.

In a further preferred embodiment, the lithium metal is used in the form of relatively coarse pieces, for example in the form of granules having edge lengths of at least 1 mm. Preference is given to a maximum edge length of the lithium pieces of 4 mm. Particularly preferably, the lithium granules used have edge lengths of from 2 to 3 mm.

In the reaction of lithium metal with the methyl halide, the methyl chloride or methyl bromide is added in metered amounts preferably over a period of from 1 to 8 hours. The reaction temperature is preferably maintained in the range from 0 to 50° C.

Because of the low density of the lithium metal of 0.54 g/ml, the excess metal that remains when the reaction is complete floats, and the remaining lithium metal can be separated from the only slightly cloudy reaction solution. The separation can be carried out, for example, by distilling off using a submersed tube. Another possible method of separating the unchanged lithium from the reaction solution consists in allowing the solution to run through a sieve, for example having a mesh size of from 0.5 to 1 mm, and washing the unchanged lithium back into the synthesis reactor with fresh solvent.

In this manner, the lithium metal does not need to be decomposed—as is conventional in the standard process—with water or the like, which is dangerous inter alia owing to the evolution of gas which occurs thereby according to $2Li + 2H_2O \rightarrow LiOH + H_2\uparrow$ Instead, it can be used, for example, for a subsequent batch for the preparation of further methyllithium. In this manner, methyllithium-lithium bromide-containing solutions (synthesis agents) having a very high LiBr concentration can be obtained in a particularly simple and economical manner.

The subject-matter of the invention is explained in greater detail by means of the following examples:

EXAMPLE 1

Preparation of a 5.5% methyllithium Solution Having a LiBr:MeLi Ratio of 0.78:1

In an argon-filled glove box, 29.6 g of anhydrous lithium-bromide were introduced into a 250 ml ISO threaded bottle. 93 g of a lithium-bromide-free 8.0% methyllithium solution in 1,1-diethoxymethane (DEM) were then added. The mixture was stirred magnetically for 3 hours; the majority of the lithium bromide had then gone into solution.

After standing for 24 hours, a clear solution had formed over a thin solids zone. A sample of the clear phase was taken and analysed as follows:

| | Analysis (mmol./g): | | |
|---|---|---|---|
| Lithium (FES) | Bromide (argentometric) | Chloride (argentometric) | Total base (acidimetric) |
| 4.50 | 1.95 | 0.09 | 2.51 |

The following solution composition is calculated therefrom:

5.5 wt. % methyllithium ⎫
16.9 wt. % lithium bromide ⎬ molar ratio LiBr:MeLi = 0.78:1
0.4 wt. % lithium chloride ⎭

Remainder: DEM

EXAMPLE 2

Preparation of a 4.3% methyllithium Solution Having a LiBr:MeLi Ratio of 0.93:1

As in Example 1, 74.5 g of a bromide-free, 8.0% methyllithium solution in DEM, 23.7 g of lithium bromide and 52 g of anhydrous DEM were mixed and stirred for two hours at room temperature. The clear supernatant phase was distilled off and analysed as follows (mmol./g):

| Li⁺ | Br⁻ | Cl⁻ | Total base | Molar ratio LiBr:MeLi |
|---|---|---|---|---|
| 3.84 | 1.80 | 0.07 | 1.94 | 0.93:1 |

The following solution composition is calculated therefrom:
4.3 wt. % MeLi
15.6 wt. % LiBr
0.3 wt. % LiCl
Remainder: DEM

EXAMPLE 3

Preparation of a 5% nethyllithium Solution Having a LiBr:MeLi Ratio of 1 by Synthesis from methyl bromide and lithium Powder in DEM In an 800 ml double-walled reactor, 11.5 g (1.66 mol.) of lithium powder (0.5% Na content) were placed in 250 g of dry DEM (water content 33 ppm) and heated to 30° C. with stirring.

Then 78 g (0.82 mol.) of gaseous methyl bromide were passed in in the course of 1.5 hours. The internal temperature was maintained at from 30 to 35° C. by counter-cooling. When the metered addition was complete, stirring was continued for one hour at 30° C. and the slightly cloudy solution containing only a small amount of lithium residues was discharged onto a glass filter frit (G3).

The filtrate was clear and slightly yellowish.

Final weighed product: 307 g

| Analysis (mmol./g): | | | |
|---|---|---|---|
| Li$^+$ | Br$^-$ | Total base | Molar ratio LiBr:MeLi |
| 4.52 | 2.20 | 2.31 | 0.95:1 |

Product composition: 5.1% MeLi, 19.1% LiBr, remainder DEM

A product yield of 86% is calculated therefrom. By flushing out the reactor and washing the filtration residue it was possible to increase the yield by a further 5%.

EXAMPLE 4

Preparation of a 6.6% methyllithium Solution Having a LiBr:MeLi ratio of 1 by Synthesis from methyl bromide and lithium Granules in DEM In the same apparatus as in Example 3, 17.2 g (2.48 mol.) of lithium metal granules (edge length approximately 3 mm) were placed in 250 g of anhydrous DEM and cooled to 10° C. with stirring. When this temperature had been reached, 106 g (1.125 mol.) of methyl bromide gas were passed in in the course of 5.5 hours and at internal temperatures of from 10 to 15° C. When the metered addition was complete, stirring was continued for 2 hours at room temperature and the suspension was then discharged onto a D1 glass filter frit.

Final weighed product: 362 g of a yellow, slightly cloudy and viscous solution

| Analysis (mmol./g): | | | |
|---|---|---|---|
| Li$^+$ | Br$^-$ | Total base | Molar ratio LiBr:MeLi |
| 5.60 | 2.84 | 2.85 | 1:1.00 |

Product composition: 6.3% MeLi, 24.7% LiBr, remainder DEM

Yield: 92% of theory

The invention claimed is:

1. A synthesis agent containing methyllithium and lithium bromide, wherein methyllithium and lithium bromide are dissolved in a solvent of formula (1)

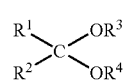

formula (I)

wherein $R^1$ and $R^2$ are independently H, Me or Et, and $R^3$ and $R^4$ are Me or Et, and the molar ratio of LiBr to MeLi is at least 0.7 and not more than 1.5; and the methyllithium concentration is at least 4 wt. %.

2. The synthesis agent according to claim 1, wherein the molar ratio of LiBr to MeLi is at least 0.8.

3. The synthesis agent according to claim 1, wherein the molar ratio of LiBr to MeLi is at least 1.0.

4. The synthesis agent according to claim 1, wherein the synthesis agent comprises from 1 to 40 wt. % of one or more aromatic solvents.

5. The synthesis agent according to claim 4, wherein the aromatic solvent comprises one or more of the substances benzene, toluene, ethylbenzene, xylene or cumene.

6. A process for the preparation of a synthesis agent containing methyllithium (MeLi) and lithium bromide in a solvent of formula (1)

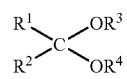

formula (I)

wherein $R^1$ and $R^2$ independently of one another are H, Me or Et, and $R^3$ and $R^4$ are Me or Et, wherein to a solution containing methyllithium and lithium bromide in a LiBr/MeLi molar ratio of <0.7 in a solvent of the general formula (1) there is added lithium bromide in an amount such that a LiBr/MeLi molar ratio of at least 0.7 and not more than 1.5 is obtained, the initial concentration of methyllithium being such that the concentration is at least 4 wt. % after addition of the lithium bromide.

7. A process for the preparation of a synthesis agent containing methyllithium (MeLi) and lithium bromide in a solvent of formula (1)

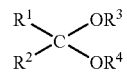

formula (I)

wherein $R^1$ and $R^2$ independently of one another are H,Me or Et,and $R^3$ and $R^4$ are Me or Et, wherein a methyl halide with the formula Me-Hal, wherein Hal is Cl or Br is reacted with lithium metal, the reaction being carried out in a solvent of formula (1) and lithium bromide being added to the solvent before the reaction, and the amounts of the substances used being so chosen that, when the reaction is complete, the concentration of dissolved methyllithium is at least 4 wt. % and the molar ratio of dissolved LiBr to dissolved MeLi is at least 0.7 and not more than 1.5.

8. The process according to claim 7, wherein the methyl halide is methyl bromide.

9. The process for the preparation of a synthesis agent containing methyllithium (MeLi) and lithium bromide in a solvent of formula (1)

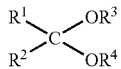

formula (I)

wherein R¹ and R² independently of one another are H, Me or Et, and R³ and R⁴ are Me or Et, wherein methyl bromide is reacted with lithium metal in the solvent of the general formula (1), and the amounts of the substances used are so chosen that, when the reaction is complete, the concentration of dissolved methyllithium is at least 4 wt. % and the molar ratio of dissolved LiBr to dissolved MeLi is at least 0.7 and not more than 1.5.

10. The process according to claim 7, wherein the lithium metal is used in the form of pieces (granules) and the lithium pieces have edge lengths of ≧1 mm.

11. The process according to claim 8, wherein the lithium metal is used in the form of pieces (granules) and the lithium pieces have edge lengths of ≧1 mm.

12. The process according to claim 9, wherein the lithium metal is used in the form of pieces (granules) and the lithium pieces have edge lengths of ≧1 mm.

13. The process according to claim 10, wherein the lithium pieces have edge lengths of from 2 to 3 mm.

14. The process according to claim 11, wherein the lithium pieces have edge lengths of from 2 to 3 mm.

15. The process according to claim 12, wherein the lithium pieces have edge lengths of from 2 to 3 mm.

16. The process according to claim 8, wherein the excess metal is separated from the dissolved MeLi.

17. The process according to claim 9, wherein the excess metal is separated from the dissolved MeLi.

18. The process according to claim 10, wherein the excess metal is separated from the dissolved MeLi.

19. The process according to claim 11, wherein the excess metal is separated from the dissolved MeLi.

20. The process according to claim 12, wherein the excess metal is separated from the dissolved MeLi.

21. The process according to claim 13, wherein the excess metal is separated from the dissolved MeLi.

22. The process according to claim 14, wherein the excess metal is separated from the dissolved MeLi.

23. The process according to claim 15, wherein the excess metal is separated from the dissolved MeLi.

24. The process according to claim 7, wherein the methyl chloride or methyl bromide is added in metered amounts over a period of from 1 to 8 hours.

25. The process according to claim 8, wherein the methyl chloride or methyl bromide is added in metered amounts over a period of from 1 to 8 hours.

26. The process according to claim 9, wherein the methyl chloride or methyl bromide is added in metered amounts over a period of from 1 to 8 hours.

27. The process according to claim 7, wherein the reaction temperature is maintained in the range from 0 to 50° C.

28. The process according to claim 8, wherein the reaction temperature is maintained in the range from 0 to 50° C.

29. The process according to claim 9, wherein the reaction temperature is maintained in the range from 0 to 50° C.

* * * * *